United States Patent
Del Soldato

(10) Patent No.: US 6,211,233 B1
(45) Date of Patent: Apr. 3, 2001

(54) PROSTAGLANDIN PHARMACEUTICAL COMPOSITIONS

(75) Inventor: Piero Del Soldato, Milan (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/423,286

(22) PCT Filed: Jun. 17, 1998

(86) PCT No.: PCT/EP98/03645

§ 371 Date: Nov. 8, 1999

§ 102(e) Date: Nov. 8, 1999

(87) PCT Pub. No.: WO98/58910

PCT Pub. Date: Dec. 30, 1998

(30) Foreign Application Priority Data

Jun. 19, 1997 (IT) .......................................... MI97A001440

(51) Int. Cl.[7] .......................... A61K 31/21; C07C 203/04
(52) U.S. Cl. .......................... 514/509; 514/468; 549/462; 558/480; 558/482; 558/483; 558/484
(58) Field of Search ............................ 549/462; 558/480, 558/482, 483, 484; 514/509, 468

(56) References Cited

U.S. PATENT DOCUMENTS 5,625,083    4/1997    Bezuglov et al. .................... 560/121

FOREIGN PATENT DOCUMENTS

| | | |
|---|---|---|
| 0 357581 | 3/1990 | (EP) . |
| 92/01668 | 6/1992 | (WO) . |
| 94 06433 | 3/1994 | (WO) . |
| 94 10141 | 5/1994 | (WO) . |
| 95 30641 | 11/1995 | (WO) . |
| 95/30641 | 11/1995 | (WO) . |

OTHER PUBLICATIONS

Hempelmann et al., "Non–synergistic relaxant effects of vasoactive intestinal polypeptide and SIN–1 in human isolated cavernous artery and corpus cavernosum" *European Journal of Pharmacology*, vol. 276, 1995, pp. 277–280.

Duarte et al., "Peripheral analgesia and activation of the nitric oxide–cyclic GMP pathway" *European Journal of Pharmacology*, vol. 186, 1990, pp. 289–293.

Stack et al., "Intracavernous Injection of Vasoactive Drugs in the Rabbit" *Urological Research* vol. 16, 455–458.

Martinez–Pineiro et al., "Cyclic Guanosine Monophosphate Mediates Penile Erection in the Rat" *Research Paper Eur Urol*, 1993, vol. 24, 492–499.

*Primary Examiner*—Bernard Dentz
(74) *Attorney, Agent, or Firm*—Arent, Fox, Kintner, Plotkin & Kahn

(57) ABSTRACT

Compounds of the general formula $A—X_1—NO_2$, or their pharmaceutical compositions, wherein A contains a prostaglandin residue, $X_1$ is a bivalent connecting bridge.

6 Claims, No Drawings

PROSTAGLANDIN PHARMACEUTICAL COMPOSITIONS

This application is a 371 of PCT/EP98/03645 filed Jun. 17, 1998.

The present invention relates to drugs to be used in male impotence.

In particular it relates to drugs which are used at lower but equally effective doses than those commonly used for the treatment of said therapy, and combined with fewer side effects, in particular as far as the absence of hypotension and algogenic activity is concerned.

It is well known in the art that the available therapies for treating male impotence are based on different approaches depending on the aetiology.

In the case of impotence due to endocrine causes treatment with testosterone is used.

In the case of impotence due to vascular alterations, or following from some neurological alterations, it is used an intracavernous injection of vasoactive compounds made by the patient himself before sexual intercourse. This method of administration allows a local pharmacological activity and reduces to a minimum any interference with the other vascular areas of the body which could lead to severe side effects including vasodilation and hypotension. The drugs more frequently used with said method include the association papaverine-phentolamine and Prostaglandin $E_1$ ($PGE_1$). This is a useful approach from the therapeutic point of view, but it has the disadvantage to presenting side effects. In fact, papaverine induces local fibrosis, prolonged erections and hepatic alterations; Prostaglandin $E_1$ induces pain in 20% of cases and prolonged erections in 1–2% of cases. $PGE_1$ is anyhow at the moment the drug most used for this type of therapy.

Besides clinical drug treatments, are well known in the art the use of prostheses and mechanical devices.

At the present time, the available drugs solve the problem only in a limited number of cases. Research is being made on the basis of various hypothesis. However, the drugs which have been proposed up to now are less active than prostaglandin-based drugs.

It was felt the need to have drugs as effective in the treatment of impotence as least as those based on prostaglandin but without presenting the side effects possessed by said known drugs as described above.

It has been surprisingly and unexpectedly found a class of drugs as herein below defined which has an improved activity than prostaglandin and the advantage of being used at lower doses with less side effects, in particular it does not cause any hypotension or algogenic activity.

It is an object of the invention the compounds, or their compositions having the general formula $$A-X_1-NO_2 \quad (I)$$

for use as medicaments, in particular as drugs for the treatment of impotence, wherein:

$$A=R(CR_aR_bO)_u(COX)_t \quad (II)$$

wherein:
- t and u are integers and are equal to 0 or 1;
- X=O, NH, $NR_{1c}$ wherein $R_{1c}$ is a linear or branched alkyl having from 1 to 10 carbon atoms;
- $R_a$ and $R_b$, equal or different from each other, are H, $C_1-C_3$ alkyl;

R is a radical having the following formula:

(III)

where $m_0$ is an integer and can have a value of 0 or 1;
where the meaning of the various substituents of formula III is as follows:

when t=1, u=0 and $m_0$=1;

$R_1$=H; an alkyl having from 1 to 6 carbon atoms, preferably from 1 to 3, or a free valence;

$R_2$=OH; O— such as to form with $R_1$, when $R_1$ is a free valence, and with the carbon atom at position 15, a group C=O, $R_3$, $R_4$, equal or different one from the other, are equal to $R_1$, or one of them is a bond O—, and the other is a free valence so that with the carbon atom $C_4$ they form a group C=O;

$R_5$, $R_6$, equal or different one from the other, are equal to $R_1$, in particular when both $R_5$ and $R_3$ are each a free valence, $R_5$ and $R_3$ form a double bond between $C_5$ and $C_6$;

$R_7$, $R_8$, $R_9$, $R_{10}$, equal or different one from the other, have the same meaning of $R_1$; when $R_7$ or $R_9$, and at the same time $R_8$ or $R_{10}$ are each a free valence, there is a double bond between $C_{13}$ and $C_{14}$;

$R_{11}$=$R_1$;

$R_{12}$=$R_{11}$ or OH;

$R_{13}$, $R_{14}$, $R_{15}$, $R_{16}$, equal or different one from the other, are equal to $R_1$; when $R_{13}$ or $R_{15}$, and at the same time $R_{14}$ or $R_{16}$, are each a free valence, there is a double bond between $C_1$ and $C_2$;

$R_{17}$, $R_{18}$, equal or different one from the other, are equal to $R_1$;

$R_{19}$, $R_{20}$, equal or different one from the other, are equal to $R_1$; when $R_6$ or $R_5$ is a free valence, and at the same time $R_{19}$ or $R_{20}$ is a free valence, there is a double bond between $C_4$ and $C_5$;

$R_{21}$, $R_{22}$, $R_{23}$, $R_{24}$, equal or different one from the other, are equal to $R_1$;

$R_{25}$, $R_{26}$, equal or different one from the other, are equal to $R_1$, but both $R_{25}$ and $R_{26}$ cannot be a free valence;

$R_{27}$ is a linear or whenever possible branched alkyl having from one to six carbon atoms;

B is equal to the group O= (a keto group with the carbon atom at position 9 of the prostaglandin molecule), OH or —O—;

when no aliphatic chain $C_7-C_2$ is found attached at position 8, in its place there is the alkylaromatic residue:

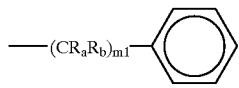 (IV)

wich is bound to formula (III) (B=—O—) in the following way:

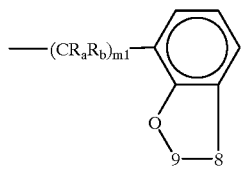 (V)

wherein $m_1$ is an integer from 1 to 6, preferably from 1 to 3;

$R_a$ and $R_b$, equal or different from each other, are as above defined;

when t=0, u=1 and $m_0$=1 the meanings of the various substituents are as above defined;

when t=0, u=0 and $m_0$=0 the meanings of the various substituents are as above defined and $C_{16}$ is bound, optionally by a bridging group —O—, to an aromatic radical or an alkyl-aril radical, where the aryl can be substituted, preferably with halogens, preferably with Cl, F; said aryl radical can also contain heteroatoms, such as O, N; the alkyl of the alkyl-aril radical is an aliphatic chain from 1 to 3 carbon atoms, preferably —$CH_2$—;

$X_1$ of formula A—$X_1$—$NO_2$ is a bivalent connecting bridge, chosen from the following:

—Y

Y is a linear or whenever possible branched C1–C20 alkylene oxygen terminated, preferably having from 2 to 5 carbon atoms or is a C5–C7 cycloalkylene oxygen terminated optionally substituted;

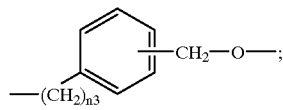

where $n_3$ is an integer from 0 to 3;

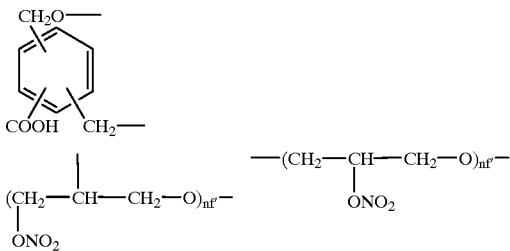

where nf' is an integer from 1 to 6, preferably from 2 to 4;

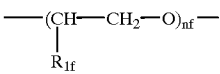

where $R_{1f}$=H, $CH_3$ and nf is an integer from 1 to 6, preferably from 2 to 4.

When in formula (II) t=1 u=0 and in formula (III) $m_0$=1, the preferred prostaglandin residues R are the following:

when B is O= (keto group with $C_9$); $R_7$, $R_8$, $R_9$ and $R_{10}$ are such as to give a double bond between $C_{13}$ and $C_{14}$; $R_2$ is OH; $R_{27}$ is $CH_3$; the substituents of the carbon atoms of the $C_2$–$C_7$ and $C_{16}$–$C_{19}$ aliphatic chains are H; R thus defined is known as the residue of Prostaglandin $E_1$;

or, by putting in the formula of Prostaglandin $E_1$ $R_2$=$CH_3$ and $R_3$, $R_4$, $R_5$, $R_6$ such as to give a double bond between $C_5$ and $C_6$;

R thus defined it is known as the residue of Arbaprostil;

or, by putting in the formula of Arbaprostil $R_7$=$R_9$=$R_9$=$R_{10}$=H; $R_1$ and $R_2$ are such as to form the group C=O with $C_{15}$; B is OH; $R_{27}$=$C_3H_7$, R thus defined it is known as the residue of Unoprostone;

or, by putting in the formula of Arbaprostil $R_{11}$=$R_{12}$=$CH_3$; $R_1$=H, R thus defined it is known as the residue of Trimoprostil;

or, when in the formula of Arbaprostil B is OH; $R_1$=H; R thus defined it is known as the residue of Prostaglandin $F_{2\alpha}$;

or, when in the formula of Prostaglandin $R_{2\alpha}$ B is O= (keto group with $C_9$), R thus defined it is known as the residue of Prostaglandin $E_2$;

or, when in the formula of Arbaprostil B is OH; R thus defined it is known as the residue of Carboprost;

or, by putting in the formula of Arbaprostil $R_1$=H; $R_{17}$=H; $R_{19}$=$CH_3$; $R_3$=$R_4$=$R_5$=$R_6$=H; $R_{27}$=$C_2H_5$; $R_{13}$=$R_{16}$=H and $R_{14}$=$R_{15}$ being free valences such as to form a double bond between C2 and C3; R thus defined it is known as the residue of Limaprost;

or, by putting in the formula of Trimoprostil $R_3$=$R_4$=$R_5$=$R_6$=H and positioning the double bond between $C_2$ and $C_3$ instead that between $C_5$ and $C_6$; R thus defined it is known as the residue of Gemeprost;

or, by putting in the formula of Arbaprostil $R_1$=$R_2$=H; $R_{12}$=OH; $R_{11}$=$CH_3$; $R_3$=$R_5$=$R_4$=$R_6$=H; R thus defined it is known as the residue of Misoprost;

or, by putting in the formula of Arbaprostil $R_1$=H; $R_{18}$=$CH_3$; $R_{27}$=$C_2H_5$; $R_3$ and $R_4$ are such that one of them is a free valence and the other is a single bond with an oxygen atom so so that together with the carbon atom $C_6$ they form a keto group C=O; R5=R6=H; R thus defined it is known as the residue of Ornoprostil;

or, as in Arbaprostil, without the $C_7$–$C_2$ aliphatic chain and the carbon atoms $C_9$–$C_8$ being linked to the group of formula (IV) as shown in (V); $R_1$=H; $R_{11}$=$CH_3$; $R_{21}$, $R_{22}$, $R_{23}$ and $R_{24}$ being each a free valence so to form a triple bond between $C_{18}$ and $C_{19}$; R thus defined it is known as the residue of Beraprost;

when t=0; u=1 and $m_0$=1: $R_a$=$R_b$=H and R is the residue of Misoprostol; R thus defined it is known as the residue of Rioprostil;

when t=1, u=0 and $m_0$=0:

when R is the residue of Arbaprostil except that $R_1$=H, $R_{19}$ or $R_{20}$ is a free valence or is H, so that between $C_4$ and $C_5$ there is a double bond; $C_{16}$ is linked to a group —O—$A_r$ wherein $A_r$=phenyl; R thus defined it is known as the residue of Enprostil;

when R is the residue of Arbaprostil except that B is OH; $R_1$=H; $C_{16}$ is linked to a group —$CH_2$—$A_r$ where $A_r$ is phenyl; it is defined a radical known as the residue of Latanaprost;

or, when in the formula of Enprostil $R_{20}$=$R_{19}$=H; it is defined a radical known as the residue of Sulprostone.

The products of the invention are obtained starting from the precursors in which R is as above defined and containing at least one carboxylic function, usually at position 2 of the corresponding formula (III); in the case of Beraprost the function —COOH is in the residue of formula (IV).

When the precursor has no free function —COOH, reactions to obtain it which are well known in the art are performed, for example by reaction of an ester or by oxidation of an alcohol.

The above substances may already exist as such (e.g. Arbaprostil, Prostaglandin $E_1$, Rioprostil, as described above).

For the precursors described in the literature, which have the carboxylic function substituted in various ways, in order to perform the synthesis according to the present invention it is preferable to start from the corresponding precursors in the acid form, i.e. bearing e free carboxylic group.

In particular, as preferred precursors one may mention Prostaglandin $E_1$, Arbaprostil, Unoprostone, Trimoprostil, Prostaglandin $F_{2\alpha}$, Prostaglandin $E_2$, Carboprost, Limaprost, Misoprostol, Gemeprost, Latanoprost, Ornoprostil, Beraprost, Enprostil, Rioprostil, Sulpostrone. These substances are prepared according to the methods described in "The Merck Index", Ed. 12, herein fully incorporated by reference.

The products of the present invention having the general formula

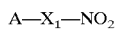

with the connecting bridge $X_1$ as above defined, are obtainable by using the methods of the known art described, for example, in WO 92/01668 and WO 95/30641, herein fully incorporated by reference. In general, the connection between A and $X_1$ is of the ester —C(O)O— type or amide —C(O)NH— or —C(O)N($R_{1c}$)— type, as defined in X of formula (II) above, and can be obtained by using known synthetic routes.

The most direct synthetic route includes reaction of acyl chlorides R—CO—Cl in halogen alcohols of the type HO—Y—Cl, HO—Y—B, HO—Y—I, Y being $X_1$ without oxygen in experimental conditions which are part of the known art.

The reaction products of formula R—CO—O—Y—Cl (Br, I) can also be obtained by reaction of the sodium or potassium salts of said acids RCOOH with dihalogen derivatives of the general formula $YCl_2$, $YBr_2$ or $YI_2$.

The reaction products are converted into the final products by reaction with $AgNO_3$, in acetonitrile, according to the known methods of literature.

The general scheme is as follows:

R—CO—Cl+HO—Y—Br→R—CO—O—Y—Br+ $AgNO_3$→A—$X_1NO_2$ where $X_1$=YO.

Another general scheme is as follows:

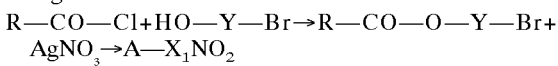
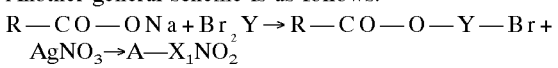

where $X_1$=YO.

In the case of amides, the synthetic sequence includes reaction of the same acyl chlorides RCOCl with aminoalcohols of the general formula:

to give amides of the general formula:

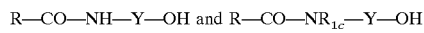

according to known methods.

The reaction of these amides with halogenating agents such as, for example, $PCl_5$, $PBr_3$, $SOCl_2$, and others, leads to halogen derivatives of the general formula:

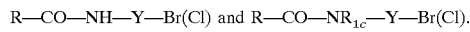

By reaction with $AgNO_3$ in acetonitrile according to methods reported in the literature, are obtained the final products A—$X_1$—$NO_2$.

The sequence of the reaction can be schematised as follows:

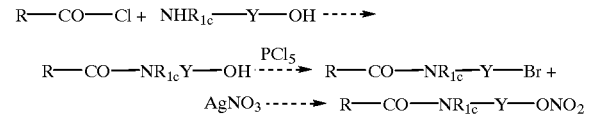

where YO is $X_1$.

An alternative route to formation of the esters is reaction of the sodium or potassium salts of the acids with the nitric esters of halogen alcohols of the general formula:

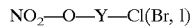

to directly give the products of the invention.

The reaction scheme is as follows:

where YO is $X_1$.

According to a further process for the preparation of the compounds of the invention the acid derivatives RCOOH are reacted with alcohols containing in the molecule a group —$ONO_2$ in the presence of aromatic sulphochlorides, in the presence of bases, such as trialkylamine, which neutralize the HCl released by the reaction.

Can also be used synthetic routes similar to those described above, where the di-halogen derivative $Br_2Y$ is reacted with —ONa. The reaction products are then converted into acetonitrile by reaction with $AgNO_3$ according to the above shown reactions.

The general scheme is shown below

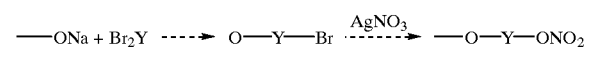

In addition to being used in the treatment of male impotence as explained at the beginning, the product of the invention can also be used in the known therapeutic applications of drugs containing prostaglandins as the active ingredient, such as in the treatment of cerebrovascular and cardiovascular disorders, glaucoma, peptic ulcer and as abortifacients.

In particular, the derivatives of Prostaglandin $E_1$ are preferred.

Following treatment of experimental animals with the new substances, no hypotension reactions nor the algogenic activity possessed by prostaglandins were observed. In fact, differently from $PGE_1$, the new derivatives of the invention were inactive in pain-induction tests.

The examples below explain the purpose of the invention and should not be understood as a limitation of same.

EXAMPLE 1

Synthesis of 2-nitroxyethyl ester of prostaglandin $E_1$

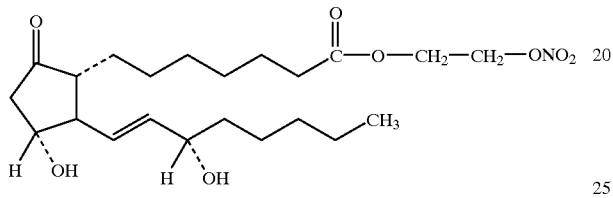

19.1 mg (0,0539 mmoles) of $PGE_1$ was dissolved in 0.7 ml of absolute acetone in a 5-ml flask. 11,5 mg (0,0604 mmol) of p-toluenesulphochloride, 12 mg (0,01188 mmoles) of triethylamine and 8 mg (0,9748 mmoles) of 2-nitroethanol were then added to the solution. The flask was closed and the reaction mixture was stirred for 22 hours at room temperature. At the end the solvent was evaporated off under vacuum, the residue was treated with 3 ml of water and the mixture was extracted with ethyl acetate three times using 7 ml each time.

The pooled organic extracts were washed with 1 ml of water and then 1,5 ml of a saturated NaCl solution. After drying over sodium sulphate, they were evaporated off to dryness under vacuum.

The oily residue which was obtained was dissolved in the lowest amount of dichloromethane and chromatographed using a small column packed with 4 g of silica gel (Silica gel 60 Å, 230–400 mesh). Dichloromethane was used as the initial eluant followed by a mixture of dichloromethane and ethyl acetate which was gradually enriched with the second component up to eluting with pure ethyl acetate. The column was then eluted with a mixture of ethylacetate/methanol, gradually enriched with methanol, up to using the pure alcohol. The fractions were analysed by TLC on silica gel (Silica Gel 60 $F_{254}$), using the eluting mixture ethyl-acetate/acetic-acid 20/0,5. The test tubes containing the reaction product were those containing the eluates with pure ethyl acetate. Said eluates were joined together and the solvent was evaporated off to obtain 6 mg of a colourless oil (yield 25%) having an Rf in the above TLC elution system equal to 0,38. The $^1$H NMR spectrum ($CD_3OD$) shows all signals corresponding to $PGE_1$ (ppm): 5 6 (m, 2H), 4–4,2(m,2H), 2,6–2,8(quartet, 1H), 2,0–2,4(m), 1,2–1,8(m). Furthermore, two multiplets centred at δ=4,75 (2H) and δ=4,4(2H) respectively, corresponding to the two methylene groups of 2-nitroethanol esterified with the carboxylic group of $PGE_1$, were observed.

I.R. spectrum: 3382 cm$^{-1}$ (OH), 2858–2930 cm$^{-1}$ (—CH—, —$CH_2$, —$CH_3$—), 1774 cm$^{-1}$ (C=O ester), 1773 cm$^{-1}$ (group C=O in a five atom ring), 1634 and 1280 cm$^{-1}$ (—O—$NO_2$). 12,4 mg (65% of the starting amount) of unreacted $PGE_1$ was recovered from the chromatographic fractions eluted with the ethylacetate/methanol mixture.

Pharmacological tests

In the pharmacological tests, the products were administered to animals by local injection in a physiological solution.

The control groups were treated with a physiological solution.

Prostaglandin $E_1$, sodium nitroprusside and SIN-1, chemically defined as 3-(4-morpholinyl)sydnone imine, which is the active metabolite of molsidomine, were used as reference products.

EXAMPLE 2

Relaxing effect in vitro on isolated human cavernosus artery and cavernosus corpus The method described by Hempelmann R. G. et al., European Journal of Pharmacology, 1995, 276, 277–280, was followed using erectile tissues from patients subjected to surgery.

The cavernosus arteries were isolated and cleaned of the surrounding connective tissue. Segments about 2-mm long were obtained and mounted in a myograph.

After building a diameter/tension curve, the artery segments were adjusted to a diameter corresponding to 90% of that reached in the presence of a trasluminal pressure of 100 mmHg. After a stabilisation period of about 60 minutes, a contraction was induced by the addition of $3\times10^{-6}$M adrenaline. After 15 minutes, the test compounds were administered at a concentration of $10^{-6}$M and the per-cent relaxation induced by the administration of the test product was recorded for each. The results are shown in Table 1.

Another set of experiments was conducted according to the same methodology, using isolated strips of cavernous tissue about 3×3×5 mm in size suspended isometrically, with application of a 5–10 mN tension in baths for isolated organs. The results are shown in Table 2.

In both experimental models an inhibitory effect of the adrenalin-induced contraction following either treatment with $PGE_1$ or administration of the nitric-acid-donor SIN-1 was found. The $PGE_1$ derivative according to the present invention is shown in the tables by the abbreviation NO-$PGE_1$.

This compound showed an effect superior to both native prostaglandin and SIN-1.

TABLE 1

Inhibitory effect of some derivatives on isolated human cavernosus artery pre-contracted with $3 \times 10^{-6}$ M adrenalin (for each treatment group n = 5 replications)

| Treatment | inhibition of contraction (%) |
| --- | --- |
| $10^{-6}$M $PGE_1$ | 19 ± 4 |
| $10^{-6}$M SIN-1 | 36 ± 7 |
| $10^{-6}$M NO-$PGE_1$ | 41 ± 9 |

TABLE 2

Inhibitory effect of some derivatives on isolated
human cavernosus tissue pre-contracted with $3 \times 10^{-6}$ M adrenaline
(for each treatment group n = 4)

| Treatment | inhibition of contraction (%) |
|---|---|
| $10^{-6}$M $PGE_1$ | 52 ± 5 |
| $3 \times 10^{-6}$M SIN-1 | 41 ± 6 |
| $10^{-6}$M NO-$PGE_1$ | 71 ± 6 |

EXAMPLE 3

Evaluation of induced erection activity and of hypotensive effect in rats

The method described by Pineiro et al., European Urology 1993, 24, 492–499, was used. Male rats weighing about 350 g (5 animals/group) were anaesthetised with urethane and maintained at a temperature of 37° C. throughout the test. The cavernosus corpuses were exteriorized by perineal section. The right cavernosus corpus was connected to a pressure transducer using a heparinised catheter and the left one was connected using a PE-10 plastic tube to a syringe by which the products were administered.

The right carotide artery was cannulated and connected to a pressure transducer to measure the systemic blood pressure. The products were administered intracavernously at a volume of 0.03 ml at a $10^{-3}$M concentration and the intracavernous pressure and systemic blood pressure were monitored. The results given in Table 3 show that $PGE_1$ was slightly active in this model, while sodium nitroprusside induced a remarkable erection activity. Both derivatives caused a drop in systemic blood pressure, which was particularly marked in the case of nitroprusside. NO-$PGE_1$ showed an effect superior to both $PGE_1$ and sodium nitroprusside on intracavernous pressure, while causing a non significant drop in systemic blood pressure, which was comparable to that of starting Prostaglandin, and was significantly lower than that of nitroprusside.

As a result, the products of the invention have been shown to possess a pharmacodynamic profile which is more favourable compared to the reference compounds.

TABLE 3

Effect of intracavernosus treatment of various
derivatives on intracavernosus pressure (P) and systematic
blood pressure (P) in anaesthetised rats (n = 4)

| Treatment | Increase in intracavernous P | Drop in systemic P (cm $H_2O$) |
|---|---|---|
| $10^{-3}$M sodium nitroprusside | 27 ± 3,7 | 51 ± 7,8 |
| $10^{-3}$M $PGE_1$ | 0,7 ± 0,4 | 18,2 ± 2,2 |
| $10^{-3}$M NO-$PGE_1$ | 36 ± 1,4 | 9,1 ± 3,1 |

EXAMPLE 4

Inducted erection activity in rabbits

The method described by Stackl W. et al., Urological Research 1988, 455–458, was used. Male rabbits weighing about 2 Kg (n. 6 animals/group) were injected 1 ml of physiological solution containing 20 μg of the test products into the right cavernosus corpus. During the injection, complete penis protrusion was observed, which was considered as 100% erection.

After injection, at pre-determined time intervals (0,5, 1,2 and 3 hours), the animals were observed for the presence of erection and evaluation of the relevant per-cent extent according to the following scheme:

0%=penis not visible

25%=glans visible

50%=penis protrusion equal to about half the complete lenght

75%=penis protrusion not complete, but greater than half the lenght

100%=complete penis protrusion

The results are given in Table 4 and show that the compound of the invention had a superior activity to that of the reference compound.

TABLE 4

Average per-cent values of extent of erection
observed at different time intervals after intracavernosus
administration of $PGE_1$, derivatives in rabbits

| Treatement | n | 30 minutes | 1 hour | 2 hours | 3 hours |
|---|---|---|---|---|---|
| Controls 4 | 6 | 0% | 0% | 0% | |
| $PGB_1$ 20 μg | 6 | 13% | 4% | 0% | |
| NO-$PGE_1$ 20 μg | 6 | 92% | 79% | 67% | 46% |

EXAMPLE 5

Effect on painful response of the compound of the invention in rats

The conventional method of Randall-Selitto modified as described in Duarte I. D. G. et al., European Journal of Pharmacology, 1990, 186, 289–293, was used to determine the potential activity on painful response of the compound. The test includes the application of a steady 20-mmHg pressure to a back paw of rats. Pressure application was discontinued when the animals appeared to react and the response latency time, which was the parameter used to evaluate the analgesic or hyperalgesic effect of the test product, was recorded. Immediately after, the product was administered by the intradermal route in the subplantar area (administration volume 2,5 μl containing 0,1 μg of the test product). The test was repeated 3 hours later.

The results given in Table 5 show that $PGE_1$ reduced the latency time, i.e. acted as a hyperalgesic agent. Sodium nitroprusside caused a slight nonsignificant increase in latency time. NO-$PGE_1$ was inactive, thus showing that the NO group in the $PGE_1$ molecule reduced the hyperalgesic property. In the table, the column identified by an "n" shows the number of animals used for each treatment.

TABLE 5

Effect of the compound of invention and reference
substances on modified Randal-Selitto test

| Product (μg/paw) | n | reaction time change (seconds) |
|---|---|---|
| $PGE_1$ (0,1) | 8 | −17 ± 2 |
| Sodium nitroprusside (5) | 8 | +4 ± 2 |
| NO-$PGE_1$ (0,1) | 10 | 0 |

The derivatives were active in various tests useful to evaluate the potential pharmacological induced-erection activity versus reference compounds.

Unlike sodium nitroprusside, the invention compounds induced no hypotension at the pharmacologically active doses in the experimental impotency models.

The invention compounds showed no pain effects which could be found after the administration of $PGE_1$ in experimental tests in rats.

What is claimed is:

1. Compounds of the formula

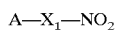

$$A—X_1—NO_2 \quad (I)$$

wherein A is

$$R(CR_aR_bO)_u(COX)_t \quad (II)$$

wherein t and u are integers and are equal to 0 or 1;

X=O, NH, $NR_{1c}$ wherein $R_{1c}$ is a linear or branched alkyl having form 1 to 10 carbon atoms;

$R_a$ and $R_b$ are equal to or different from each other and are H, or a $C_1$-$C_3$ alkyl radical and R is a radical having the following formula:

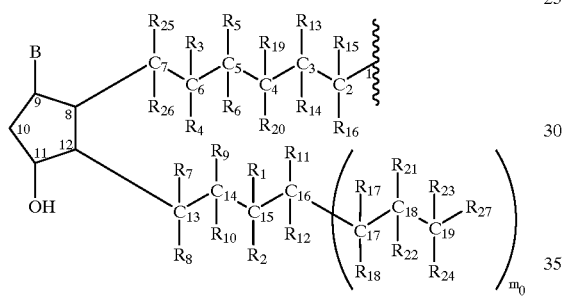

(III)

wherein $m_0$ is an integer having a value of 0 or 1; and when t=1, u=0 and $m_0$=1:

$R_1$=H; an alkyl having from 1 to 6 carbon atoms or a free valance;

$R_2$=OH, O— such as to form with $R_1$ when $R_1$ is a free valance, and with the carbon atom at position 15 a C=O group;

$R_3$ and $R_4$ are equal to or different from one another and are equal to $R_1$ or one of them is a bond O—, and the other is a free valance so that with the carbon atom $C_6$ they form a C=O group;

$R_5$ and $R_6$ are equal to or different from one another, and are equal to $R_1$ when both $R_5$ and $R_3$ are each a free valence, $R_5$ and $R_3$ form a double bond between $C_5$ and $C_6$;

$R_7$, $R_8$, $R_9$, and $R_{10}$ are equal to or different from each other, and have the same meaning as $R_1$;

when $R_7$ or $R_9$, and at the same time $R_8$ or $R_{10}$ are each a free valence, there is a double bond between $C_{13}$ and $C_{14}$;

$R_{11}$=$R_1$;

$R_{12}$=$R_{11}$ or OH;

$R_{13}$, $R_{14}$, $R_{15}$, and $R_{16}$ are equal to or different from each other, and are equal to $R_1$; when $R_{13}$ or $R_{15}$, and at the same time $R_{14}$ or $R_{16}$, are each a free valence, there is a double bond between $C_3$ and $C_2$;

$R_{17}$ and $R_{18}$ are equal to or different from each other and are equal to $R_1$;

$R_{19}$ and $R_{20}$ are equal to or different from each other and are equal to $R_1$; when $R_6$ or $R_5$ is a free valence, and $R_{19}$ or $R_{20}$ is a free valence, there is a double bond between $C_4$ and $C_5$;

$R_{21}$, $R_{22}$, $R_{23}$, and $R_{24}$ are equal to or different from each other and are equal to $R_1$;

$R_{25}$ and $R_{26}$ are equal to or different from each other and are equal to $R_1$, but both $R_{25}$ and $R_{26}$ cannot be a free valence, $R_{27}$ is a linear or branched alkyl having one to six carbon atoms;

B is equal to the group O— (a keto group with the carbon atom at position 9 of the prostaglandin molecule) or is OH or —O—;

when no aliphatic chain $C_7$-$C_2$ is at position 8, there is in its place an alkylaromatic residue:

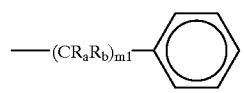

(IV)

which is bound to formula (III) (B=—O—) in the following way:

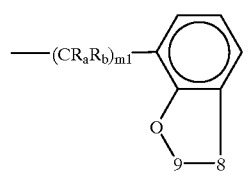

(V)

wherein $m_1$ is an integer from 1 to 6, $R_a$ and $R_b$ are equal to or different from each other, and are as defined above, when t=0, u=1, and $m_0$=1 the meanings of the various substituents are as defined above, when t=1, u=0, and $m_0$=0 the meanings of the various substituents are as defined above and $C_{16}$ is bound, optionally by a bridging group —O—, to an aromatic radical or an alkyl-aryl radical, where the aryl can be substituted, said aryl radical can also contain heteroatoms, such as O or N; the alkyl of the alkyl-aryl radical is an aliphatic chain from 1 to 3 carbon atoms;

$X_1$ of formula A—$X_1$—$NO_2$ is a bivalent connecting bridge, chosen from the following:

—Y where Y is a linear or whenever possible branched $C_1$-$C_{20}$ alkylene oxygen terminated, or is a $C_5$-$C_7$ cycloalkylene oxygen terminated optionally substituted;

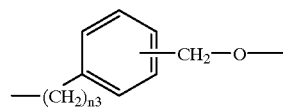

where $n_3$ is an integer from 0 to 3;

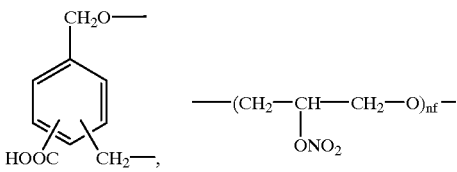

where nf is an integer from 1 to 6; and

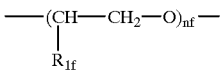

where $R_{1f}$=H or $CH_3$, and nf is an integer from 1 to 6.

2. Compounds according to claim 1 wherein the prostaglandin residues R are the following:

when in formula (II) t=1 u=0 and in formula (III) $m_0$=1:

B is O= (keto group with $C_9$); $R_7$, $R_8$, $R_9$ and $R_{10}$ are such as to given a double bond between $C_{13}$ and $C_{14}$; $R_2$ is OH; $R_{27}$ is $CH_3$; the substituents of the carbon atoms of the $C_2$–$C_7$ and $C_{16}$–$C_{19}$ aliphatic chains are H; R thus defined is known as the residue of Prostaglandin $E_1$;

or, by putting in the formula of Prostaglandin $E_1$, $R_1$=$CH_3$ and $R_3$, $R_4$, $R_5$, $R_6$ such as to give a double bond between $C_5$ and $C_6$; R thus defined is known as the residue of Arbaprostil;

or, by putting in the formula of Arbaprostil $R_7$=$R_8$=$R_9$=$R_{10}$=H; $R_1$ and $R_2$ are such as to form the group C=O with $C_{15}$; B is OH; $R_{27}$=$C_3H_7$; R thus defined is known as the residue of Unoprostone;

or, by putting in the formula of Arbaprostil $R_{11}$=$R_{12}$=$CH_3$, $R_1$=H, R thus defined s known as the residue of Trimoprostil;

or, when in the formula of Arbaprostil B is OH; $R_1$=H; R thus defined is known as the residue of Prostaglandin $F_{2\alpha}$;

or, when in the formula of Prostaglandin $F_{2\alpha}$ B is O= (keto group with $C_9$); R thus defined is known as the residue of Prostaglandin $R_2$;

or, when in the formula of Arbaprostil B is OH; R thus defined is known as the residue of Carboprost;

or, by putting in the formula of Arbaprostil $R_1$=H; $R_{17}$=H; $R_{19}$=$CH_3$; $R_3$=$R_4$=$R_5$=$R_6$=H; $R_{27}$=$C_2H_5$; $R_{13}$=$R_{16}$=H and $R_{14}$=$R_{15}$ being free valences such as to form a double bond between $C_2$ and $C_3$; R thus defined is known as the residue of Limaprost;

or, by putting in the formula of Trimoprostil $R_3$=$R_4$=$R_5$=$R_6$=H, and positioning the double bond between $C_2$ and $C_3$ instead that between $C_5$ and $C_6$; R thus defined is known as the residue of Gemeprost;

or, by putting in the formula of Arbaprostil $R_1$=$R_2$=H; $R_{12}$=OH; $R_{11}$=$CH_3$, $R_3$=$R_5$=$R_4$=$R_6$=H; R thus defined is known as the residue of Misoprost;

or, by putting in the formula of Arbaprostil $R_1$=H; $R_{18}$=$CH_3$; $R_{27}$=$C_2H_5$; $R_3$ and $R_4$ are such that one of them is a free valence and the other is a single bond with an oxygen atom so that together with the carbon atom $C_6$ form a keto group C=O; R5=R6=H, R thus defined is known as the residue of Ornoprostil;

or, as in Arbaprostil, without the $C_7$–$C_2$ aliphatic chain and the carbon atoms $C_9$–$C_8$ linked to the group of formula (IV) as shown in (V); $R_1$=H; $R_{11}$=$CH_3$; $R_{21}$, $R_{22}$, $R_{23}$, $R_{24}$ being each a free valence to form a triple bond between $C_{18}$ and $C_{19}$; R thus defined is known as the residue of Beraprost;

when t=0; u=1 and $m_0$=1: $R_a$=$R_b$=H and R is the residue of Misoprostol, R thus defined is known as the residue of Rioprostil, when t=1, u=0 and $m_0$=0:

when R is the residue of Arbaprostil except that $R_1$=H; $R_{19}$ or $R_{20}$ is a free valence or H, so that between $C_4$ and $C_5$ there is a double bond; $C_{16}$ is linked to a group —O—$A_r$ wherein $A_r$=phenyl; R thus defined is known as the residue of Enprostil;

when R is the residue of Arbaprostil except that B is OH; $R_1$=H; $C_{16}$ is linked to a group —$CH_2$—$A_r$ where $A_r$ is phenyl; it is defined a radical known as the residue of Latanaprost;

when in the formula of Enprostil $R_{20}$=$R_{19}$=H; it is defined a radical known as the residue of Sulprostone.

3. A compound according to claim 1 where R is the residue of Prostaglandin $E_1$.

4. A method for treating cerebrovascular and cardiovascular disorders, glaucoma, and peptic ulcer disorders, and a method for inducing abortion, comprising administering to a patient an effective amount of a compound of claim 1.

5. Pharmaceutical compositions containing as the active ingredient compounds of claim 1 and a pharmaceutically acceptable carrier.

6. A method for treating impotence comprising administering to a patient an effective amount of a compound of the formula:

wherein A is

wherein t and u are integers and are equal to 0 or 1;

X=O, NH, $NR_{1c}$ wherein $R_{1c}$ is a linear or branched alkyl having form 1 to 10 carbon atoms;

$R_a$ and $R_b$ are equal to or different from each other and are H, or a $C_1$–$C_3$ alkyl radical and R is a radical having the following formula:

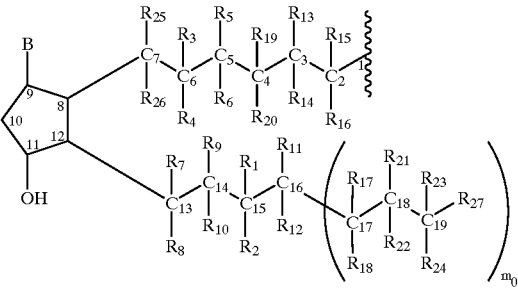

wherein $m_0$ is an integer having a value of 0 or 1; and when t=1, u=0 and $m_0$=1:

$R_1$=H; an alkyl having from 1 to 6 carbon atoms or a free valance;

$R_2$=OH, O— such as to form with $R_1$ when $R_1$ is a free valance, and with the carbon atom at position 15 a C=O group;

$R_3$ and $R_4$ are equal to or different from one another and are equal to $R_1$ or one of them is a bond O—, and the other is a free valance so that with the carbon atom $C_6$ they form a C=O group;

$R_5$ and $R_6$ are equal to or different from one another, and are equal to $R_1$ when both $R_5$ and $R_3$ are each a free valence, $R_5$ and $R_3$ form a double bond between $C_5$ and $C_6$;

$R_7$, $R_8$, $R_9$, and $R_{10}$ are equal to or different from each other, and have the same meaning as $R_1$;

when $R_7$ or $R_9$, and at the same time $R_8$ or $R_{10}$ are each a free valence, there is a double bond between $C_{13}$ and $C_{14}$;

$R_{11}=R_1$;

$R_{12}=R_{11}$ or OH;

$R_{13}$, $R_{14}$, $R_{15}$, and $R_{16}$ are equal to or different from each other, and are equal to $R_1$; when $R_{13}$ or $R_{15}$, and at the same time $R_{14}$ or $R_{16}$, are each a free valence, there is a double bond between $C_3$ and $C_2$;

$R_{17}$ and $R_{18}$ are equal to or different from each other and are equal to $R_1$;

$R_{19}$ and $R_{20}$ are equal to or different from each other and are equal to $R_1$; when $R_6$ or $R_5$ is a free valence, and $R_{19}$ or $R_{20}$ is a free valence, there is a double bond between $C_4$ and $C_5$;

$R_{21}$, $R_{22}$, $R_{23}$, and $R_{24}$ are equal to or different from each other and are equal to $R_1$;

$R_{25}$ and $R_{26}$ are equal to or different from each other and are equal to $R_1$, but both $R_{25}$ and $R_{26}$ cannot be a free valence, $R_{27}$ is a linear or branched alkyl having one to six carbon atoms;

B is equal to the group O= (a keto group with the carbon atom at position 9 of the prostaglandin molecule) or is OH or —O—;

when no aliphatic chain $C_7$–$C_2$ is at position 8, there is in its place an alkylaromatic residue:

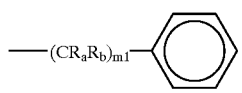
(IV)

which is bound to formula III (B=—O—) in the following way:

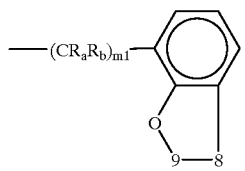
(V)

wherein $m_1$ is an integer from 1 to 6, $R_a$ and $R_b$, are equal to or different from each other, and are as defined above, when t=0, u=1, and $m_0$=1 the meanings of the various substituents are as defined above, when t=1, u=0, and $m_0$=0 the meanings of the various substituents are as defined above and $C_{16}$ is bound, optionally by a bridging group —O—, to an aromatic radical or an alkyl-aryl radical, where the aryl can be substituted, said aryl radical can also contain heteroatoms, such as O or N; the alkyl of the alkyl-aryl radical is an aliphatic chain from 1 to 3 carbon atoms;

$X_1$ of formula A—$X_1$—$NO_2$ is a bivalent connecting bridge, chosen from the following:

—Y where Y is a linear or whenever possible branched $C_1$–$C_{20}$ alkylene oxygen terminated, or is a $C_5$–$C_7$ cycloalkylene oxygen terminated optionally substituted;

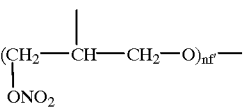

where $n_3$ is an integer from 0 to 3;

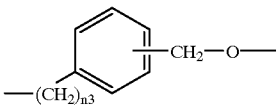

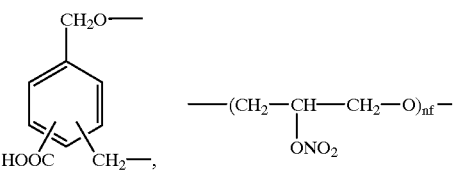

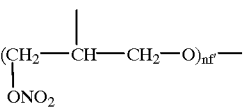

where nf' is an integer from 1 to 6; and

—(CH—$CH_2$—O)$_{nf}$—
  |
  $R_{1f}$ where $R_{1f}$=H or $CH_3$, and nf is an integer from 1 to 6.

* * * * *